United States Patent [19]

Van der Knaap

[11] Patent Number: Plant 6,741

[45] Date of Patent: Apr. 18, 1989

[54] CHRYSANTHEMUM PLANT NAMED BRIDESMAID

[75] Inventor: Jacques C. M. Van der Knaap, De Lier, Netherlands

[73] Assignee: Fides Beheer B.V., De Lier, Netherlands

[21] Appl. No.: 124,545

[22] Filed: Nov. 23, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Bridesmaid having white ray florets formed from tubes, flat capitulum form, single anemone capitulum type, and diameter of inflorescence of 40–50 mm.

1 Drawing Sheet

The present invention comprises a new and distinct cultivar of *Chrysanthemum morifolium,* hereinafter referred to by the cultivar name Bridesmaid.

Bridesmaid is a product of a planned breeding program which had the objective of creating new Chrysanthemum cultivars with single (anemone) capitulum type, white ray florets, nine (9) weeks response, large numbers of flowers along the stem, and the ability to produce commercially acceptable quality in year around cut mum programs. Such traits in combination were not present or needed improvement in previously available commercial cultivars.

Bridesmaid was originated from a hybridization made by applicant in a controlled breeding program in De Lier, Holland in 1979. The female parent was Smile. The male parent of Bridesmaid was White Marguerite, an unpatented and former commercial cultivar.

Bridesmaid was discovered and selected by applicant as one flowering plant within the progeny of the stated parentage by applicant in June 1979 in a controlled environment in De Lier, Holland.

The first act of asexual reproduction of Bridesmaid was accomplished when vegetative cuttings were taken from the initial selection in August 1979 in a controlled environment in De Lier, Holland by a technician working under formulations established and supervised by applicant. Horticultural examination of selected units initiated in March 1980 has demonstrated that the combination of characteristics as herein disclosed for Bridesmaid are firmly fixed and are retained through successive generations of asexual reproduction.

Bridesmaid has not been observed under all possible environmental conditions. The phenotype may vary significantly with variations in environment such as temperature, light intensity, and day length. The following observations, measurements and comparisons describe plants grown in De Lier, Holland under greenhouse conditions which approximate those generally used in commercial practice.

The following traits have been repeatedly observed and are determined to be basic characteristics of Bridesmaid, which in combination distinguish this Chrysanthemum as a new and distinct cultivar:

1. Flat capitulum form.
2. Single (anemone) capitulum type.
3. White ray florets, which are produced during maturing of the flower from tubes. Thus, prior to fully opening, the flowers resemble spider-like inflorescence.

4. Diameter across the face of the capitulum is 40–50 mm.
5. Yellow-green cushion (immature) to yellow (mature) disc florets.

Of the many commercial cultivars known to the present inventor, the most similar in comparison to Bridesmaid is Smile. In comparison to Smile, Bridesmaid has more vigor, no compound spray, more cream white ray floret color, and the production of numerous flowers along the stem. The capitulum form and capitulum type are similar to those same characteristics of Smile.

The accompanying photographic drawing shows in front view typical inflorescnece and foliage characteristics of Bridesmaid, with colors being as nearly true as possible with illustrations of this type.

In the following description, color references are made to the Royal Horticultural Society Colour Chart. The color values were determined between 11:00 a.m. and 12:00 noon in April 1980 under natural daylight at De Lier, Holland.

Classification:

*Botanical.*—*Chrysanthemum morifolium,* Ramat., cv. Bridesmaid.

*Commercial.*—Cut anemone spray.

INFLORESCENCE

A. Capitulum:
- *Form.*—Flat.
- *Type.*—Anemone, with flat mature ray florets being formed from tubes.
- *Diameter across face.*—40–50 mm.

B. Corolla of ray florets:
- *Color (general tonality from a distance of three meters).*—White.
- *Color (upper surface).*—155D.

C. Corolla of disc florets:
- *Color (mature).*—Yellow-green.
- *Color (immature).*—Yellow.

D. Reproductive organs:
- *Androecium.*—Present only in some disc florets; few.
- *Gynoecium.*—Present in both disc and ray florets; numerous.

PLANT

A. General appearance:
- *Height.*—100 cm.

B. Foliage:

*Color* (*upper surface*).—167A.
*Color* (*under surface*).—167B.
*Shape.*—Strongly indented.

I claim:

1. A new and distinct cultivar of Chrysanthemum plant named Bridesmaid, as illustrated and described, and parts thereof.

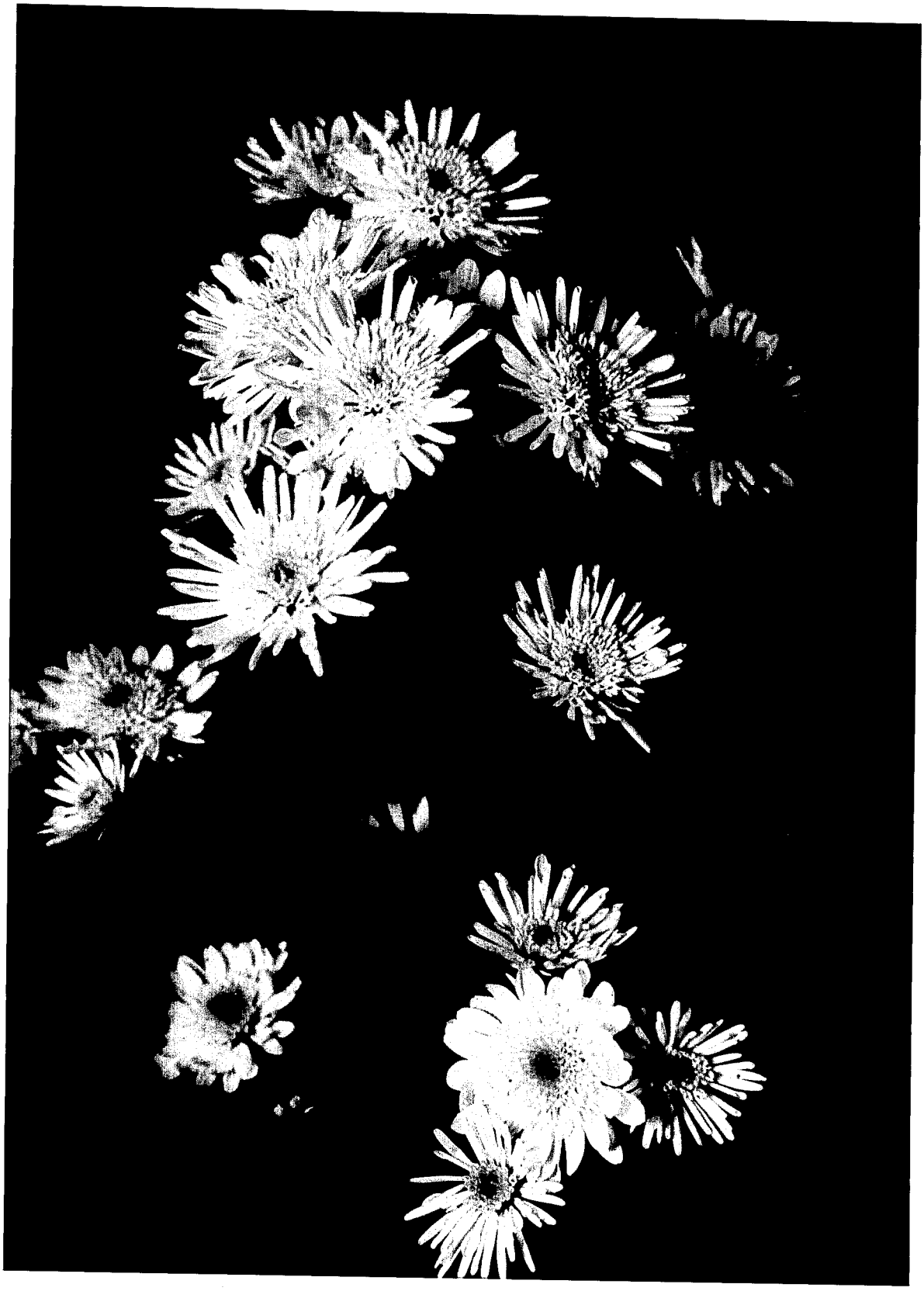

* * * * *